United States Patent
Knecht et al.

(10) Patent No.: US 11,304,750 B2
(45) Date of Patent: Apr. 19, 2022

(54) LOW-TEMPERATURE PLASMA CATHETER FOR LESS-INVASIVE, LOCALIZED TREATMENT OF ENDOCARDITIS AND ATHEROSCLEROSIS

(71) Applicant: The Penn State Research Foundation, University Park, PA (US)

(72) Inventors: Sean David Knecht, State College, PA (US); Christopher A. Siedlecki, Harrisburg, PA (US); Sven Gunnar Bilen, State College, PA (US); Michael Matthew Micci, Lemont, PA (US); Ian Gilchrist, Hummelstown, PA (US); Girish Soorappa Kirimanjeswara, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 72 days.

(21) Appl. No.: 16/637,168

(22) PCT Filed: Aug. 9, 2018

(86) PCT No.: PCT/US2018/046027
§ 371 (c)(1),
(2) Date: Feb. 6, 2020

(87) PCT Pub. No.: WO2019/032838
PCT Pub. Date: Feb. 14, 2019

(65) Prior Publication Data
US 2020/0229867 A1 Jul. 23, 2020

Related U.S. Application Data

(60) Provisional application No. 62/543,174, filed on Aug. 9, 2017.

(51) Int. Cl.
*A61B 18/14* (2006.01)
*A61N 1/44* (2006.01)
(Continued)

(52) U.S. Cl.
CPC ............ *A61B 18/1492* (2013.01); *A61N 1/44* (2013.01); *A61B 2018/0041* (2013.01);
(Continued)

(58) Field of Classification Search
CPC ........ H05H 2245/30; A61B 2018/0041; A61B 18/1492; A61B 2018/00357;
(Continued)

(56) References Cited

U.S. PATENT DOCUMENTS 6,206,878 B1 * 3/2001 Bishop ................. A61B 18/042
219/121.55
6,210,410 B1 * 4/2001 Farin ..................... A61B 1/018
219/121.51
(Continued)

OTHER PUBLICATIONS

Mikhailov, V. Development and Clinical Applications of Intravenous Laser Blood Irradiation ILBI. Laser Therapy, vol. 18, No. 2, 2009, pp. 69-83; p. 72, col. 2, paragraph 6.
International Search Report dated Oct. 3, 2018; International Application No. PCT/US2018/046027.

*Primary Examiner* — Jaymi E Della
(74) *Attorney, Agent, or Firm* — Dinsmore & Shohl, LLP

(57) ABSTRACT

Various aspects of the invention relate to methods and devices for treating diseases and conditions including atherosclerosis and endocarditis using low-temperature, non-equilibrium plasmas. A device may be, for example, a catheter that carries electrodes and a dielectric material for generating a localized, non-equilibrium plasma in a bodily fluid such as blood.

16 Claims, 7 Drawing Sheets

(51) Int. Cl.
*A61B 18/00* (2006.01)
*A61B 18/12* (2006.01)
*A61B 18/04* (2006.01)

(52) U.S. Cl.
CPC ............ *A61B 2018/00083* (2013.01); *A61B 2018/00357* (2013.01); *A61B 2018/00583* (2013.01); *A61B 2018/00714* (2013.01); *A61B 2018/00982* (2013.01); *A61B 2018/046* (2013.01); *A61B 2018/122* (2013.01); *A61B 2018/147* (2013.01); *A61B 2018/1475* (2013.01); *H05H 2245/30* (2021.05)

(58) Field of Classification Search
CPC .... A61B 2018/00583; A61B 2018/122; A61B 18/042
See application file for complete search history.

(56) References Cited

U.S. PATENT DOCUMENTS

| | | | |
|---|---|---|---|
| 6,780,178 B2* | 8/2004 | Palanker | A61B 18/14 606/34 |
| 7,220,261 B2 | 5/2007 | Truckai et al. | |
| 2001/0001314 A1* | 5/2001 | Davison | A61B 18/1492 606/41 |
| 2003/0146310 A1* | 8/2003 | Jackson | B01J 19/088 239/690 |
| 2009/0188626 A1* | 7/2009 | Lu | H05H 1/2406 156/345.35 |
| 2013/0006229 A1* | 1/2013 | Delaney | A61B 18/042 606/15 |
| 2015/0283392 A1 | 10/2015 | Bourke, Jr. et al. | |
| 2016/0113700 A1* | 4/2016 | Hancock | A61B 18/148 606/29 |
| 2019/0343572 A1* | 11/2019 | Schulz | H05H 1/46 |

* cited by examiner

LOW-TEMPERATURE PLASMA CATHETER FOR LESS-INVASIVE, LOCALIZED TREATMENT OF ENDOCARDITIS AND ATHEROSCLEROSIS

CROSS REFERENCE TO RELATED APPLICATIONS

This application is a National Phase Entry of International Application No. PCT/US2018/46027, entitled "LOW-TEMPERATURE PLASMA CATHETER FOR LESS-INVASIVE, LOCALIZED TREATMENT OF ENDOCARDITIS AND ATHEROSCLEROSIS" and filed Aug. 9, 2018, which claims priority to U.S. Provisional Patent Application Ser. No. 62/543,174, filed Aug. 9, 2017 and entitled "LOW-TEMPERATURE PLASMA CATHETER FOR LESS-INVASIVE, LOCALIZED TREATMENT OF ENDOCARDITIS AND ATHEROSCLEROSIS," both of which are incorporated herein by reference in their respective entireties.

GOVERNMENT SPONSORSHIP

This invention was made with government support under Grant No. EB024693 awarded by the National Institutes of Health and under Hatch Act Project Nos. PEN04446 and PEN04605 awarded by the United States Department of Agriculture The Government has certain rights in the invention.

BACKGROUND

Cardiovascular disease is the number one killer of men and women in the United States. Cardiovascular disease is primarily caused by the accumulation of arterial plaque (atherosclerosis), which reduces blood flow. Methods exist to remove this plaque such as by balloon angioplasty or excimer laser angioplasty or by a mechanical means such as a rotablator. A common complication of these methods is restenosis, which is the renarrowing of the arterial pathways as a result of scar tissue produced in arterial walls following an intervention. Restenosis complicates the foregoing methods and results in a potentially poor long-term prognosis. An ongoing need therefore exists for improved methods to remove atherosclerotic plaque without damaging artery walls.

SUMMARY

Various aspects of the disclosure relate to a method of treating a disease or condition in a subject, comprising contacting the subject with a low-temperature, non-equilibrium plasma catheter, and producing a localized, non-equilibrium plasma in a bodily fluid of the subject. The localized, non-equilibrium plasma may be produced adjacent to a structure that is associated with a disease or condition, such as atherosclerosis or a biofilm, for example, to produce reactive oxygen species (ROS) and/or reactive nitrogen species (RNS) that ablate a portion or all of the structure, kill a pathogen, and/or provide a therapeutic effect. A method typically does not produce or otherwise release gas within the subject, and a method typically does not appreciably increase the temperature of the bodily fluid.

The non-equilibrium plasma may be, for example, a corona discharge, spark discharge, or streamer discharge in which the electrons of the non-equilibrium plasma have higher energies than ions and uncharged molecules. In certain embodiments, the non-equilibrium plasma is a corona discharge.

Various aspects of the disclosure relate to a device for administering a non-equilibrium plasma to a subject, comprising a catheter, a first electrode, a first wire, a second electrode, a second wire, a dielectric material, and at least one insulating sheath. A catheter typically comprises a lumen and an aperture. A first electrode and a second electrode are typically carried within the lumen of a catheter and capable of carrying a voltage of at least 1 kV such as at least 10 kV. A dielectric material is typically carried within the lumen of the catheter and in electrical communication with a first electrode and a second electrode such that the dielectric material is capable of spatially-orienting a non-equilibrium plasma between the first electrode and the second electrode. A dielectric material may be configured to exit the lumen of a catheter through an aperture of the catheter. A first wire may be connected to a first electrode, and a second wire may be connected to a second electrode. A first wire and second wire are typically at least partially disposed within the lumen of a catheter and surrounded by at least one insulating sheath.

DETAILED DESCRIPTION

Figure 1A:
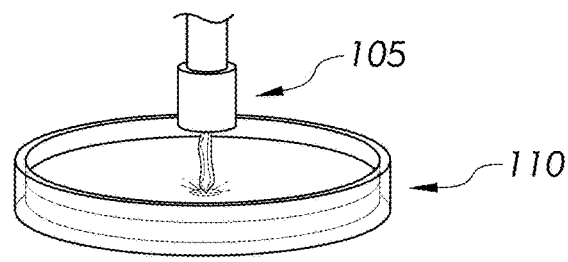
FIG. 1A shows cultured *S. aureus* bacteria on an agar plate exposed to a low-temperature plasma jet.

Various aspects of the disclosure relate to the finding that low-temperature, non-equilibrium plasma generated in blood does not result in significant coagulation or blood cell lysis. Low-temperature, non-equilibrium plasma may therefore provide a strategy to break apart disease-associated structures in the vasculature of a subject. Accordingly, low-temperature, non-equilibrium plasma may be suitable to ablate atherosclerotic plaque and other disease-associated structures in the cardiovascular system. A low-temperature, non-equilibrium plasma may be suitable to kill one or more pathogens (e.g., bacteria and viruses) in the cardiovascular system.

Low-temperature corona discharge generates plasma, for example, which is an ionized fluid produced through the application of high voltages on small electrode systems to gases or liquids. The resulting electric field accelerates electrons until they collide with atoms or molecules in these fluids. Effects of these collisions depend on the kinetic energy of the electrons. At sufficient energies, the collisions can result in the liberation of an electron from the atom/molecule, i.e., ionization. At lower energies, electron collisions can result in the breaking of molecular bonds and the excitation of bound electrons in atoms/molecules resulting in the generation of chemically-reactive species. Due to high pressures (~1 atm) and small sizes (~ mm or less) of the low-temperature non-equilibrium plasma, the large number of collisions distributes the electron energy to many more massive particles. This keeps the temperature of the massive particles near ambient temperature. The minimal thermal effect of low-temperature, non-equilibrium plasma indicates that it can be applied to living tissue without risking thermal damage.

In some aspects, the invention relates to a medical device for administering a non-equilibrium plasma to a subject. A device typically includes a catheter having a lumen and a distal aperture. Catheters of the invention are generally catheters configured to enter a blood vessel of a subject, especially an artery or vein, such as a femoral artery, radial artery, femoral vein, internal jugular vein, or subclavian vein. A distal aperture as defined herein is an aperture configured to enter a subject. The distal aperture allows a dielectric material, first electrode, and/or second electrode to exit a catheter, e.g., to administer a non-equilibrium plasma to a subject.

A device typically includes a first electrode and a second electrode. The first electrode and second electrode may be carried within the lumen of a catheter, e.g., such that the first electrode and second electrode may be partially or completely expelled from the lumen through the distal aperture of the catheter and optionally retracted back into the lumen of the catheter through the distal aperture. The first electrode may be carried within the lumen of a catheter, and the second electrode may cover a surface within the catheter. The first electrode and second electrode may comprise, for example, platinum or tungsten. A dielectric coating may optionally cover at least a portion of the first electrode and/or second electrode. In some embodiments, the first electrode and/or second electrode lacks a dielectric coating.

The distance between a first electrode and a second electrode is typically less than 10 mm while the device is in use. For example, a distance between a first electrode and a second electrode may be about 10 μm to about 10 mm, such as about 100 μm to about 5 mm, or about 500 μm to about 2 mm. The distance between a first electrode and second electrode may be fixed or the distance may be adjustable, e.g., to retract one or both of a first electrode and a second electrode while the device is not being used to generate a non-equilibrium plasma.

The electrode that is the cathode typically has a diameter of about 50 nm to about 10 μm such as about 50 nm to about 200 nm, about 100 nm to about 500 nm, about 200 nm to about 700 nm, or about 500 nm to about 1 μm. The electrode that is the cathode may nevertheless have a diameter of 1 mm or less such as about 500 μm or less or about 100 μm or less.

The electrode that is the cathode typically has a radius of curvature of about 25 nm to about 5 μm such as about 25 nm to about 100 nm, about 50 nm to about 250 nm, about 100 nm to about 350 nm, or about 250 nm to about 200 nm. The electrode that is the cathode may nevertheless have a diameter of 500 μm or less such as about 250 μm or less or about 50 μm or less.

The electrode that is the anode typically has a diameter of about 50 nm to about 10 μm such as about 50 nm to about 200 nm, about 100 nm to about 500 nm, about 200 nm to about 700 nm, or about 500 nm to about 1 μm. The electrode that is the anode may nevertheless have a diameter of 1 mm or less such as about 500 μm or less or about 100 μm or less.

The electrode that is the anode typically has a radius of curvature of about 25 nm to about 5 μm such as about 25 nm to about 100 nm, about 50 nm to about 250 nm, about 100 nm to about 350 nm, or about 250 nm to about 200 nm. The electrode that is the anode may nevertheless have a diameter of 500 μm or less such as about 250 μm or less or about 50 μm or less.

The first electrode and/or the second electrode may be partially coated with an insulating coat. An insulating coat may comprise aluminum oxide, parylene, or both aluminum oxide and parylene. The insulating coat may have a thickness of about 10 nm to about 10 μm such as about 20 nm to about 200 nm, about 100 nm to about 500 nm, about 250 nm to about 750 nm, about 500 nm to about 1 μm, or about 1 μm to about 5 μm.

An insulating coat is preferably conformal with the first electrode and/or second electrode. A conformal insulating coat may be formed, for example, by atomic layer deposition or physical vapor deposition. An insulating coat may be formed, for example, by atomic layer deposition or physical vapor deposition.

The first electrode and the second electrode may each be a needle, and the first electrode and the second electrode may have a path of shortest approach that occurs either at the tip of each needle or near the tip of each needle.

The first electrode and the second electrode may be coaxial. For example, the second electrode may partially or wholly surround the length of the first electrode. When the second electrode partially surrounds the first electrode, the second electrode can optionally be a mesh, e.g., such as a mesh anode. The first electrode may be the cathode, and the second electrode may be the anode. In this configuration, an insulating coat, insulating layer, and/or insulating sheath is preferably disposed between the first electrode and the second electrode to favor discharges at the ends of each electrode.

In some embodiments, both the first electrode and the second electrode can operate as either a cathode or an anode, or the first electrode is the anode and the second electrode is the cathode.

A device typically includes a dielectric material. The dielectric material may be carried within the lumen of a catheter, and the dielectric material is typically configured to exit the lumen of the catheter through a distal aperture. For example, the device may be configured such that the dielectric material may be partially or completely expelled from the lumen of the catheter through the distal aperture of the catheter and optionally retracted back into the lumen of the catheter through the distal aperture. The dielectric material is typically in electrical communication with the first electrode and the second electrode such that the dielectric material is capable of spatially-orienting a non-equilibrium plasma between the first electrode and the second electrode.

The term "spatially-orienting," as used herein, refers to the ability of a dielectric material to define the shortest conductive path between a first electrode and a second electrode such that a non-equilibrium plasma between the first electrode and the second electrode occurs at substantially the same location relative to the dielectric material each time the non-equilibrium plasma is produced. The ability of a dielectric material to spatially-orient a non-equilibrium plasma may allow a physician or other operator of a device described herein to generate a localized, non-equilibrium plasma in close proximity to a structure that the physician or operator desires to ablate. Similarly, the ability of a dielectric material to spatially-orient a non-equilibrium plasma may allow a physician or other operator of a device described herein to generate a localized, non-equilibrium plasma oriented away from structures that the physician or operator wishes to protect from ablation.

A dielectric material may comprise a glass, a biocompatible polymer, or a multi-layer combination of a glass and/or biocompatible polymer. For example, the dielectric material may comprise or consist of quartz, polytetrafluoroethylene, sapphire, ruby, garnet, silica, cerium(IV) oxide, yttria-stabilized zirconia, alumina, corundum, silicon carbide, boron nitride, parylene, or polyurethane. The dielectric material typically has a dielectric strength of at least about 5 kV/mm, such as at least about 10, 11, 12, 13, 14, 15, 16, 17, 18, 19, 20, 100, or 1000 kV/mm.

The dielectric material may have a dielectric strength of about 5 to about 5000 kV/mm, such as about 10 to about 5000, about 20 to about 1000, about 20 to about 250, about 100 to about 1000, about 100 to about 200, about 1000 to about 3000, about 2000 to about 4000, or about 3000 to about 5000 kV/mm. The dielectric material typically has a relative permittivity of less than about 15, such as less than or equal to about 14, 13, 12, 11, 10, 9, 8, 7, 6, or 5. The dielectric material may have a relative permittivity of 1 to about 12, such as about 1.2 to about 10, or about 2 to about 8.

A dielectric material of the invention lacks a gas inlet. A dielectric material of the invention also typically lacks any other features to administer a gas plasma that are not also useful to deliver a low-temperature, non-equilibrium plasma in a liquid.

A device typically includes a first wire connected to a first electrode and a second wire connected to a second electrode, wherein the first wire and the second wire are capable of carrying an electric current, and the first wire and the second wire are disposed within the lumen of the catheter (e.g., from about the distal aperture of the catheter to a proximal aperture, from which the first wire and the second wire typically exit the catheter). A first wire has a distal end (e.g., which is connected to a first electrode) and a proximal end (e.g., which is optionally connected to a high-voltage pulse generator). A second wire has a distal end (e.g., which is connected to a second electrode) and a proximal end (e.g., which is optionally connected to a high-voltage pulse generator). A catheter may have a proximal aperture, and a first wire and a second wire may exit the lumen of a catheter through the proximal aperture. A proximal aperture, as defined herein, is an aperture that is not configured to enter a subject, thereby allowing a physician or other operator of a medical device described herein to access, manipulate, and use the components carried within the catheter.

The first electrode may optionally be part of the first wire, e.g., the first electrode may be the tip or end of the first wire.

The second electrode may optionally be part of the second wire, e.g., the second electrode may be the tip or end of the second wire.

A first wire and a second wire typically have a diameter of about 1 µm to about 1 mm, such as about 1 µm to about 500 µm, about 5 µm to about 250 µm, about 10 µm to about 150 µm, about 10 µm to about 50 µm, about 20 µm to about 75 µm, about 50 µm to about 100 µm, about 75 µm to about 150 µm, about 100 µm to about 200 µm, about 150 µm to about 300 µm, or about 250 µm to about 500 µm. A first wire and a second wire typically have a length long enough to connect a high-voltage pulse generator to a first electrode and a second electrode associated with a catheter within a subject. A first wire and second wire may be, for example, at least about 0.5 m long, such as at least about 1 m, 1.5 m, or 2 m long. The upper limit for the length of a first wire and a second wire is not particularly limiting.

A first wire and a second wire are typically metal such as tungsten, copper, aluminum, or stainless steel. For example, a first wire may be an anode and comprise copper or aluminum, and a second wire may be a cathode and comprise tungsten.

A device typically includes at least one insulating layer, such as at least one insulating sheath, wherein the at least one insulating layer surrounds the length of a first wire and a second wire thereby preventing the flow of electric current between either the first wire or the second wire and any other component within the catheter other than an electrode. Portions of the insulating layer that may come into contact with a subject or a bodily fluid of the subject are preferably biocompatible, and polyurethane is generally considered biocompatible during cardiovascular procedures. The insulating sheath may comprise, for example, polyurethane, or the insulating sheath may consist essentially of polyurethane. An insulating sheath may be, for example, about 0.5 mm to about 5 mm thick.

A device of the invention lacks a gas line for fueling a gas plasma.

A device may optionally comprise a pulse generator for generating electric pulses, e.g., a high-voltage pulse generator. In various embodiments, however, a device lacks a pulse generator, e.g., a device may be configured for use with a pulse generator rather than being connected to a pulse generator. A pulse generator may be connected to a proximal end of a first wire and a proximal end of a second wire. A pulse generator typically controls the magnitude, width, shape, and repetition rate of a voltage pulse supplied to a first electrode and second electrode. Suitable pulse generators are known (see. e.g., PCT Patent Application Publication No. WO 2015/073921, herein incorporated by reference in its entirety) and commercially available, for example, from Eagle Harbor Technologies (Seattle, Wash. US). The parameters of the pulse generator are typically capable of producing a low-temperature, non-equilibrium plasma in a liquid, e.g., when connected to a first wire and a second wire of a device described herein. A pulse generator may be capable of supplying a voltage of about 1 kV to about 100 kV, with a pulse width of about 1 ns to about 1 µs, and/or a repetition rate of about 1 Hz to about 20 kHz. The pulse generator may be capable of supplying a sub-nanosecond pulse. The pulse generator may be capable of producing a repetition rate greater than 20 kHz. A pulse generator may be capable of supplying a voltage of about 1 kV to about 30 kV, a pulse width of about 10 ns to about 500 ns, and a repetition frequency of about 1 Hz to about 20 kHz.

A device may further include a liquid line disposed within the lumen of a catheter. A liquid line may be configured to deliver a liquid at or adjacent to a site of a non-equilibrium plasma. The liquid may comprise any pharmaceutically-acceptable carrier such as saline. The liquid may optionally comprise one or more drugs such as an anti-inflammatory drug, an anti-coagulant, and/or an antibiotic. A liquid line may irrigate the site of a non-equilibrium plasma to remove ablated matter. A liquid line may dilute a bodily fluid at the site of a non-equilibrium plasma to inhibit damage to the components of the bodily fluid such as cells, platelets, and/or macromolecules.

A device may further include at least one optic fiber disposed within the lumen of a catheter. The at least one optic fiber may be configured to illuminate and/or transmit images (e.g., video) of a non-equilibrium plasma, the environment surrounding the non-equilibrium plasma, and/or a dielectric material. An optic fiber may allow visualization of the positioning and orientation of a dielectric material and/or electrodes within a subject.

A method may comprise monitoring the location of a dielectric material, first electrode, and/or second electrode, e.g., via video and/or ultrasound.

A device may further include an aspiration line disposed within the lumen of a catheter. An aspiration line may allow the removal of material ablated from a subject. A device comprising an aspiration line typically also includes a liquid line, e.g., to replace liquid that is aspirated from a subject.

Various aspects relate to a method of treating a disease or condition in a subject. The disease or condition may be atherosclerosis or endocarditis. A method may include contacting a subject with a low-temperature, non-equilibrium plasma catheter (e.g., such as a catheter described herein). A method may include producing a localized, non-equilibrium plasma in a bodily fluid of the subject. The term "bodily fluid," as used herein, refers to a liquid, liquid suspension, or liquid colloid of a subject such as blood.

A subject may be a human, rodent, lagomorph, feline, canine, porcine, ovine, bovine, equine, or primate. In certain embodiments, the subject is a human having cardiovascular disease such as cardiovascular disease that is associated with an increased risk of ischemia. A subject may present with atherosclerosis, an embolism, a thrombus, or a cardiovascular biofilm. A subject may have an implanted medical device, such as a stent, which is associated with a biofilm. In certain embodiments, the subject is a human having endocarditis such as endocarditis that is associated with a biofilm. A subject may have a permanent indwelling device (i.e., wherein "permanent" refers to a device that is intended to remain in the subject for at least one month such as at least one year or for the remaining lifetime of the subject).

The production of a localized, non-equilibrium plasma typically ablates either a structure associated with a disease or condition or a portion of the structure, or the localized, non-equilibrium plasma generates a reactive molecule or ion, and the reactive molecule or ion ablates either a structure associated with the disease or condition or a portion of the structure. The structure may comprise atheromatous plaque, fibroatheroma, arterial fibrosis, an atherosclerotic lesion, a fatty-acid streak, low-density lipoprotein (LDL) particles, a thrombus, fibrin, a calcium deposit, or a biofilm, e.g., the structure may be atherosclerotic plaque or may be associated with atherosclerotic plaque or the structure may be associated with a bacterial infection. The nature of the structure is not particularly limiting so long as the location of the structure is accessible by catheterization.

While it may be theoretically desirable to ablate an entire atherosclerotic lesion or biofilm, in practice, it may be preferable to simply ablate a portion of a structure, e.g., to reduce the amount of trauma to the tissue adjacent to the structure and/or to reduce the risk of damage to the integrity of a blood vessel wall. The mere partial opening of an occluded coronary artery may have a profound beneficial effect on the quality of life and life expectancy of a subject even if the artery remains partially occluded. Similarly, the partial ablation of a biofilm may allow bacterial colonization to be subsequently controlled by antibiotics and/or a subject's own immune response.

A localized, non-equilibrium plasma typically generates a reactive molecule or ion. A reactive molecule or ion may be a reactive oxygen species (ROS) or a reactive nitrogen species (RNS). ROS and RNS species include $H_2O_2$ (hydrogen peroxide), .OH (hydroxyl radical), $O_2.^-$ (superoxide anion radical), $O_3$ (ozone), $.O_2$ (singlet oxygen), O (monomeric oxygen), $NO_2^-$ (nitrite), $NO_3^-$ (nitrate), nitric oxide (NO), and $ONOO^-$ (peroxynitrite) among others. A reactive molecule or ion typically ablates either a structure associated with the disease or condition or portion of the structure. For example, the generation of a localized, non-equilibrium plasma may generate ROS that chemically react with molecules of a structure thereby degrading the structure.

In some embodiments, the localized, non-equilibrium plasma generates a therapeutic molecule. The therapeutic molecule may cause vasodilation, e.g., localized vasodilation. The therapeutic molecule may decrease muscle contractility. The therapeutic molecule may be toxic to a bacterium or other pathogen. The therapeutic molecule may be, for example, nitric oxide. In some embodiments, the therapeutic molecule activates guanylate cyclase. The therapeutic molecule may increase intracellular cyclic guanosine monophosphate ("cGMP"), e.g., in cells in close proximity to the localized, non-equilibrium plasma, e.g., within about 1 mm to 5 cm of the localized, non-equilibrium plasma. In some embodiments, the therapeutic molecule binds a transition metal ion such as iron or copper, e.g., as a ligand of a metal coordination complex. The transition metal ion may be the metal of a porphyrin (e.g., heme), cytochrome, or enzyme.

The localized, non-equilibrium plasma typically does not generate significant heat or gas. The method preferably does not increase the temperature of the bodily fluid by more than 5° C. for a period of time greater than 1 minute after the localized, non-equilibrium plasma is produced. For example, the method may not increase the temperature of the bodily fluid by more than 4° C. 3° C., 2° C., or 1° C. for more than 60 seconds, 30 seconds, 20 seconds, 10 seconds, 5 seconds, 2 seconds, or 1 second after the localized, non-equilibrium plasma is produced. The method preferably does not release a gas into the subject or otherwise produce a gas in the subject. The release of gas into the blood of a subject risks an air embolism, which can cause ischemia or stroke. The method preferably does not generate more than 1 mL of gas in a subject, such as less than 500 µL, less than 100 µL, less than 50 µL, less than 10 µL, or less than 5 µL. The method may result in the generation of essentially no gas. Preferably, the method does not generate an air embolism in the subject.

A localized, non-equilibrium plasma typically includes a series of voltage pulses. The pulse magnitude, shape, width (duration), and repetition rate (frequency) control the reactive species generated by the localized, non-equilibrium plasma. The repetition rate of a voltage pulse may be about 0.1 Hz to about 20 kHz, such as about 1 Hz to about 1 kHz, about 1 Hz to about 10 Hz, about 5 Hz to about 50 Hz, about 10 Hz to about 100 Hz, about 50 Hz to about 500 Hz, about 100 Hz to about 1 kHz, about 500 Hz to about 5 kHz, about 1 kHz to about 10 kHz. or about 2 kHz to about 20 kHz. In some embodiments, the repetition rate of the voltage pulse is greater than 20 kHz. The pulse-width of a voltage pulse may be about 100 ps to about 100 µs, such as about 100 ps to about 10 ns, about 1 ns to about 100 ns, about 10 ns to about 1 µs, about 100 ns to about 10 µs, about 1 µs to about 100 µs, about 100 ps to about 5 ns, about 500 ps to about 10 ns, about 1 ns to about 25 ns, about 10 ns to about 50 ns, about 25 ns to about 75 ns, about 50 ns to about 100 ns, about 75 ns to about 150 ns, about 100 ns to about 200 ns, about 150 ns to about 300 ns, about 250 ns to about 500 ns, about 400 ns to about 800 ns, about 500 ns to about 1 µs, about 750 ns to about 1.5 µs, about 1 µs to about 2 µs, about 1.5 µs to about 3 µs, about 2.5 µs to about 5 µs, about 4 is to about 8 µs, about 5 µs to about 10 µs, about 7.5 µs to about 15 µs, or about 10 µs to about 20 µs. The voltage of a localized, non-equilibrium plasma may be about 1 kV to about 100 kV such as about 1 kV to about 75 kV, about 1 kV to about 50 kV, or about 1 kV to about 30 kV.

A localized, non-equilibrium plasma may have an electron density of greater than $10^{22}$ electrons per cubic meter, such as at least about $10^{13}$ electrons per cubic meter or at least about $10^{24}$ electrons per cubic meter. A localized, non-equilibrium plasma may have an electron density of about $10^{22}$ to about $10^{28}$ electrons per cubic meter, such as about $10^{23}$ to about $10^{27}$ electrons per cubic meter or about $10^{24}$ to about $10^{26}$ electrons per cubic meter.

A localized, non-equilibrium plasma may have a power density of greater than $10^{12}$ watts per cubic meter, such as at least about $10^{13}$ watts per cubic meter or at least about $10^{14}$ watts per cubic meter. A localized, non-equilibrium plasma may have a power density of about $10^{12}$ to about $10^{16}$ watts per cubic meter such as about $10^{13}$ to about $10^{15}$ watts per cubic meter.

A localized, non-equilibrium plasma may have an electric field greater than 100 kV per cm, such as at least about 200 kV per cm or at least about 500 kV per cm. A localized, non-equilibrium plasma may have an electric field of about 100 to about 10.000 kV per cm, such as about 200 to about 5,000 kV per cm or about 500 to about 2,000 kV per cm.

EXEMPLIFICATION

Example 1. Ablation of *S. aureus* Bacteria with Low-Temperature Plasma

Figure 1B:
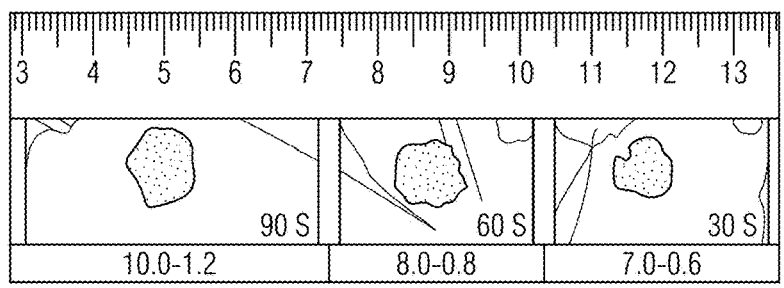
FIG. 1B shows that the zone of inhibition increases with increasing exposure time to the low-temperature plasma jet from 30 seconds ("30 S"; right-most image) to 90 seconds ("90 S"; left-most image).

*S. aureus* was exposed to a gas-phase low-temperature plasma jet configuration consisting of a 0.25 inch inner diameter polycarbonate tube surrounding a 2 mm diameter stainless steel high-voltage pin electrode with a brass ring electrode outside the tube acting as a ground electrode. Helium gas flowed at a rate of 7.5 standard liters per minute between the pin electrode and the plastic tube, and sinusoidal voltage waveforms up to 3.5 kV with a frequency of 5 kHz were applied across the electrodes. The resulting low-temperature plasma jet 105, shown FIG. 1A, was applied to a culture 110 of the bacteria for exposure times of up to 90 seconds. The results, shown in FIG. 1B, demonstrate the destruction of the bacteria at 30 seconds with an increasing zone of inhibition up to 90 seconds. These results indicate the effectiveness of low-temperature plasma in bacterial destruction through reactive low-temperature plasma-induced chemistry, most likely ROS.

Example 2. Low-Temperature Plasma has No Apparent Deleterious Effect on Blood

A low-temperature plasma system was developed that utilizes very short (10's of ns duration), high-voltage (10's of kV) pulses at a repetition rate of 1 Hz using electrodes with very small dimensions (≈125 µm diameter tungsten wire). In air or transparent liquids, the low-temperature plasma discharge is easily observable as visible radiation in the discharge region between the electrodes. Though the voltages used in this work were relatively high, the total energy was relatively small due to the extremely short pulse width. This, combined with appropriate electrode insulation, reduces the shock hazard from a low-temperature plasma.

Initial experiments used 15 mL of sheep blood in bacteriological-grade petri dishes, submerging the electrodes and exposing the blood to low-temperature plasma for a specified "dose," defined as a specific number of voltage pulses. Two low-temperature plasma experiments and one control were utilized. Doses of 60 and 180 pulses were performed on the blood samples. The control received no pulses from electrodes submerged for 180 seconds. Blood naturally reduces the ability for optical observation of low-temperature plasma discharge, but dim flashes were observed in the 60 pulse experiment and distortion of the liquid (a common observation when low-temperature plasma is produced in liquids) was observed in the 180 pulse experiment indicating that low-temperature plasma was generated during these experiments.

Coagulation time for each of the samples was found to be nearly the same across all samples indicating that the testing did not initiate the coagulation cascade under test conditions. Hematocrit remained the same before and after the application of low-temperature plasma with no measurable free hemoglobin, which suggests that the red blood cells of the blood remained intact. Platelet aggregation evaluation suggested that there may have been a mild reduction in platelet aggregation corresponding to increasing low-temperature plasma doses, though the observed effect was small and requires additional investigation. Overall, this experiment suggests the possibility of generating low-temperature plasma in blood without significant detrimental effects to blood component structure and function.

Figure 2:
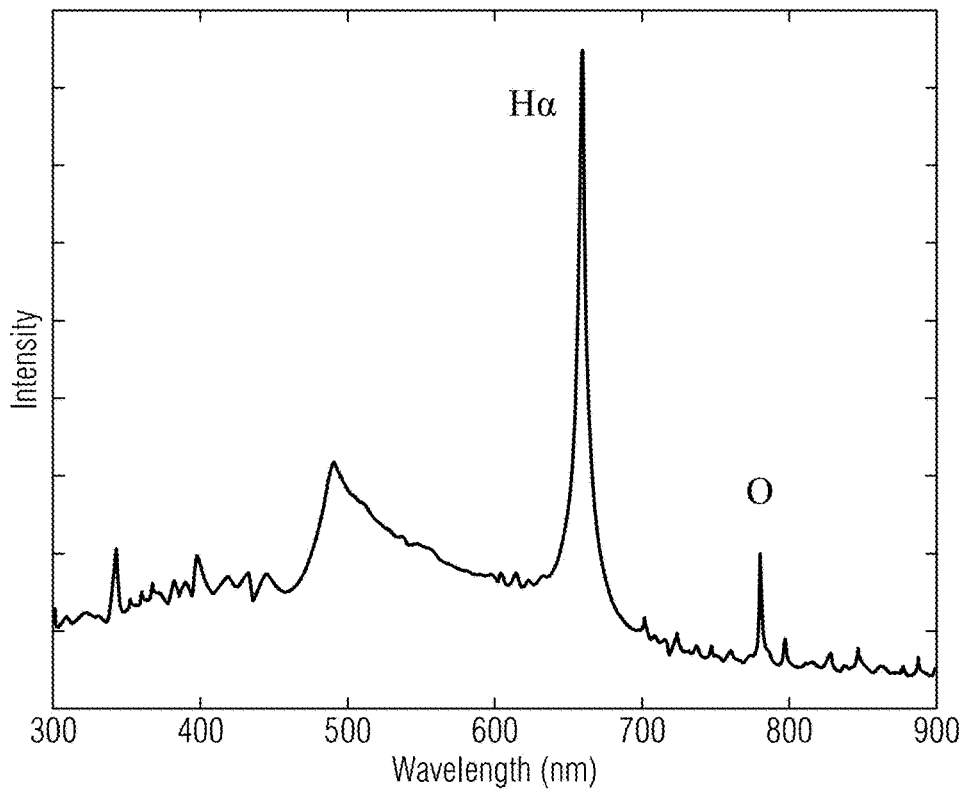
FIG. 2 is a graph of a measured optical emission spectrum from low-temperature plasma generated in water indicating that the plasma generated atomic oxygen, which is a reactive oxygen species.

Other experiments with low-temperature plasma generated in water, a primary component of human whole blood, indicate that atomic oxygen, a type of ROS, is produced as measured with a fiber-coupled, time-integrated HR2000 spectrometer ($\lambda \approx 777$ nm), as shown in FIG. 2. The larger peak at $\lambda = 656$ nm is the Balmer alpha atomic hydrogen emission that is expected in a water-generated low-temperature plasma. This indicates that the production of ROS, the expected bactericidal agent, is likely to occur in blood.

Example 3. Design and Fabrication of Electrodes Sized to Fit the Lumen of a Catheter Electrode miniaturization will be conducted through a combination of computer-aided design (CAD) solid modeling with SolidWorks, computational modeling of electric fields generated by applying voltage to different electrodes, and dielectric barrier configurations using COMSOL Multiphysics finite element software.

Figure 3:
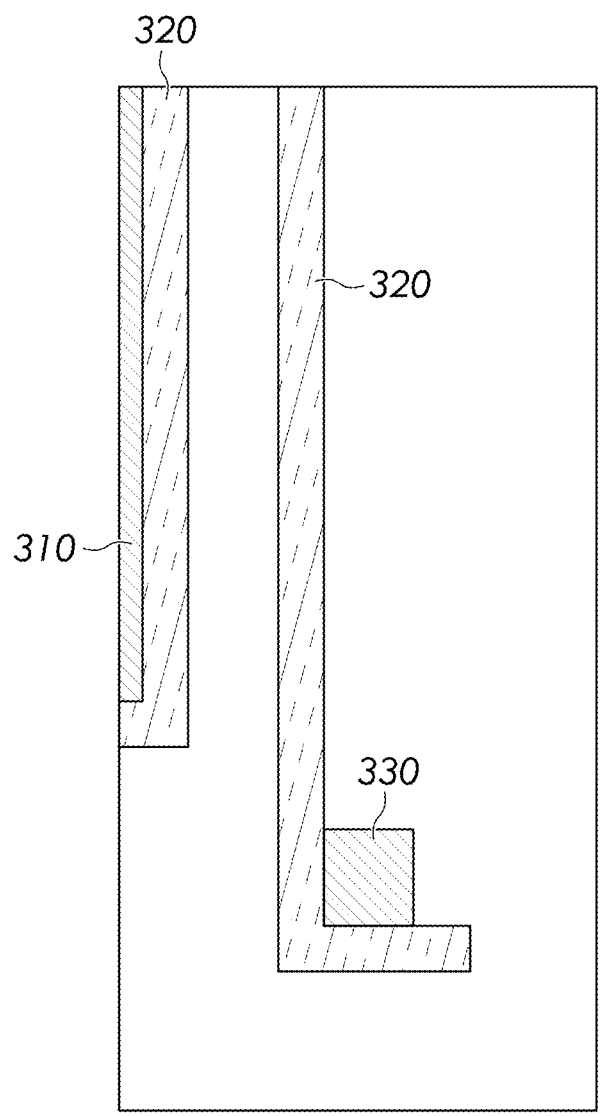
FIG. 3 is an image of a COMSOL simulation of an electric field distribution of a two-dimensional axisymmetric dielectric barrier discharge electrode configuration.

Miniaturized electrodes will be designed based on the optimum configuration determined from in vitro experiments with dimensions in the 10's of microns in diameter and 100's of microns in length, sufficiently small for integration with a catheter. The exact dimensions including the thickness of a dielectric material and spacing between high-voltage and ground electrodes will be determined using COMSOL to maximize the electric field for a given applied voltage, as shown in FIG. 3, which shows a radial surface plot of the electric field in a two-dimensional axisymmetric electrode configuration where increasing lightness indicates higher electric fields. Electrodes (e.g., a high voltage electrode 310 and a ground electrode 330) will be built through the deposition of different conducting (e.g., platinum or tungsten) and dielectric materials 320 (e.g., silicon dioxide).

The miniaturized electrodes 310, 330 will then be tested in saline and whole blood to determine that the miniaturization process still effectively creates ROS and/or RNS without a significant negative impact on blood constituents. The effect on bacterial biofilms will be determined with consideration given to the increased time necessary to clear a given surface area of bacteria. Future low-temperature plasma treatments of bacterial biofilms will occur in similar or less time than a surgical intervention.

Example 4. Catheter Tip with Mesh Electrode

Figure 4:
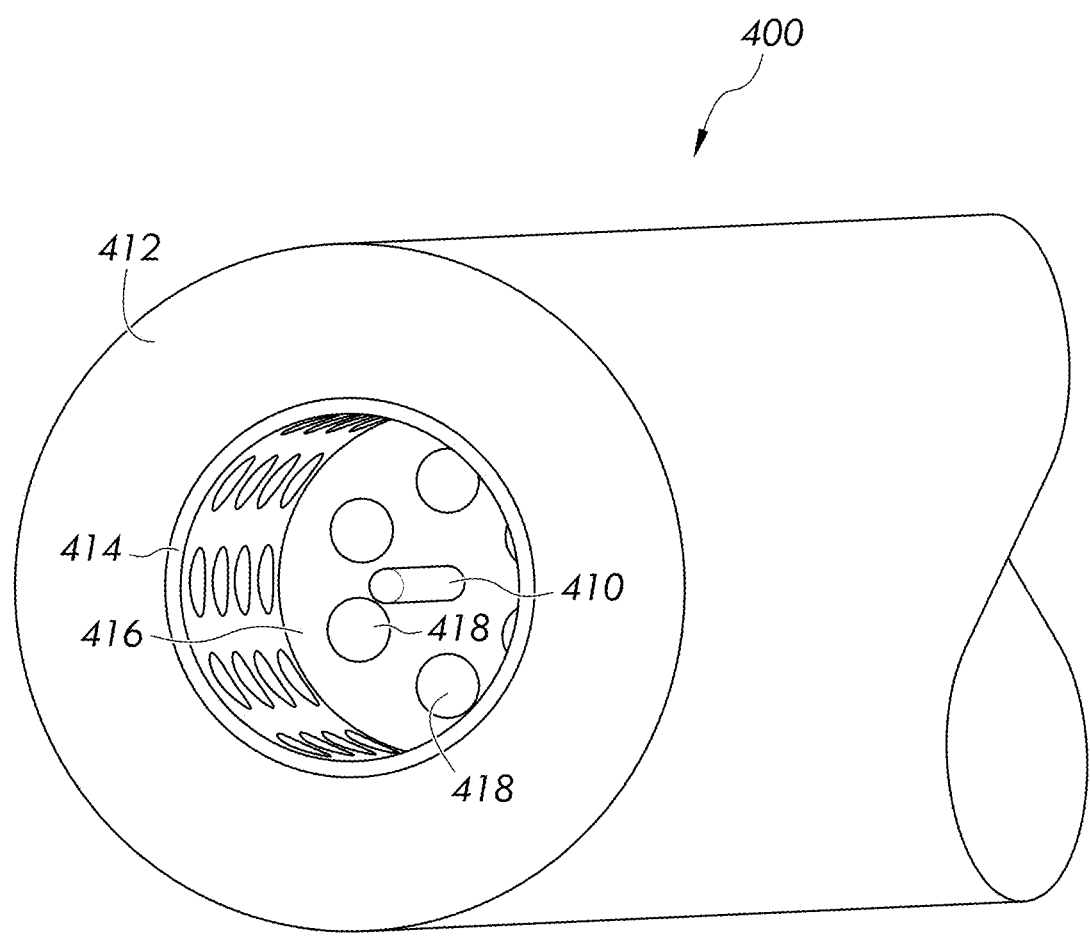
FIG. 4 is a model of a catheter tip comprising a mesh outer electrode.
Figure 6:
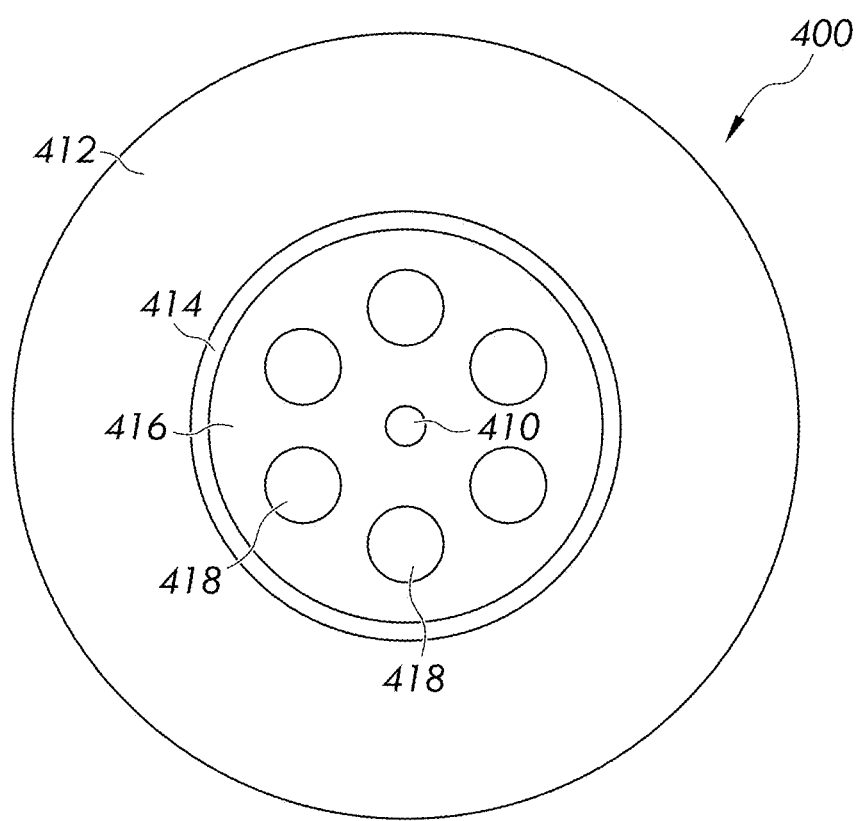
FIG. 6 is head-on view of a model of a catheter tip.

FIG. 4 is a drawing of a contemplated catheter tip 400 having a mesh outer electrode 414. An internal electrode 410 is shown in FIG. 4 surrounded by a biocompatible dielectric coating 416 with ports 418 to allow a variety of activities including saline/antibiotic transport, aspiration, and fiber optic imaging. An outer mesh electrode 414 is shown in FIG. 4 that is surrounded by a thicker, biocompatible dielectric coating 412. The relative size of the various features shown in FIG. 4 is not to scale; the depicted sizes were instead selected to enhance visualization. The shape of the mesh/ports and the placement of the ports in FIG. 4 are arbitrary and not shape- or location-dependent. The inner and outer electrodes 410, 414 depicted in FIG. 4 may also be coated with a dielectric thin film. The approximate overall diameter of the catheter 400 is on the order of millimeters. A head-on view of the catheter tip 400 is shown in FIG. 6; the head-on view is does not show features that distinguish a mesh outer electrode from a solid outer electrode.

Example 5. Catheter Tip with Solid Electrode

Figure 5:
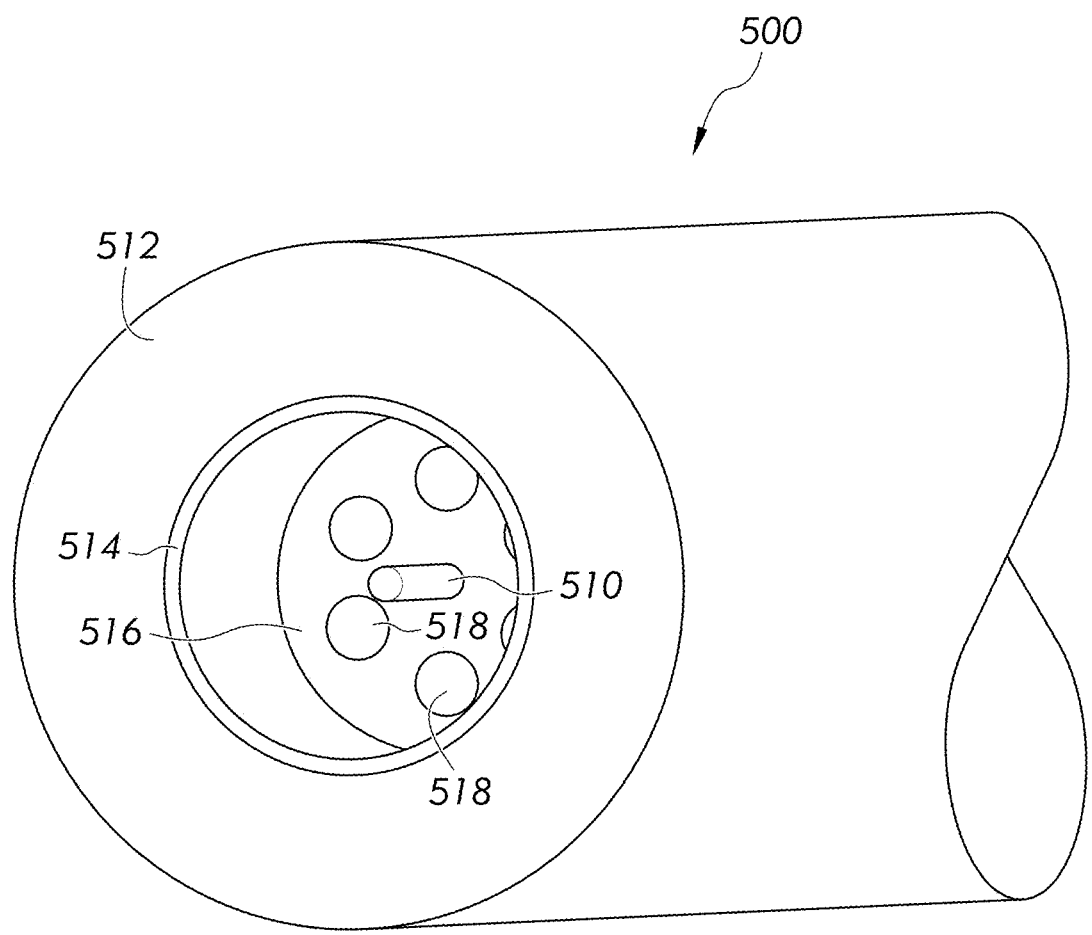
FIG. 5 is a model of a catheter tip comprising a solid outer electrode.

FIG. 5 is a drawing of a contemplated catheter tip 500 having a solid outer electrode 514. An internal electrode 510 is shown in FIG. 5 surrounded by a biocompatible dielectric coating 516 with ports 518 to allow a variety of activities including saline/antibiotic transport, aspiration, and fiber optic imaging. An outer solid electrode 514 is shown in FIG. 5 that is surrounded by a thicker, biocompatible dielectric coating 512. The relative size of the various features shown in FIG. 5 is not to scale; the depicted sizes were instead selected to enhance visualization. The shape of the ports and the placement of the ports in FIG. 5 are arbitrary and not shape- or location-dependent. The inner and outer electrodes 510, 514 depicted in FIG. 5 may also be coated with a dielectric thin film. The approximate overall diameter of the catheter 500 is on the order of millimeters. A head-on view of the catheter tip 500 is similar to that shown in FIG. 6; the head-on view is does not show features that distinguish a mesh outer electrode from a solid outer electrode.

Example 6. Plasma Discharges in Aqueous Liquids

Figure 7:
FIG. 7 is an image of a streamer plasma discharge generated with a sharpened tungsten needle in distilled water.
Figure 8:
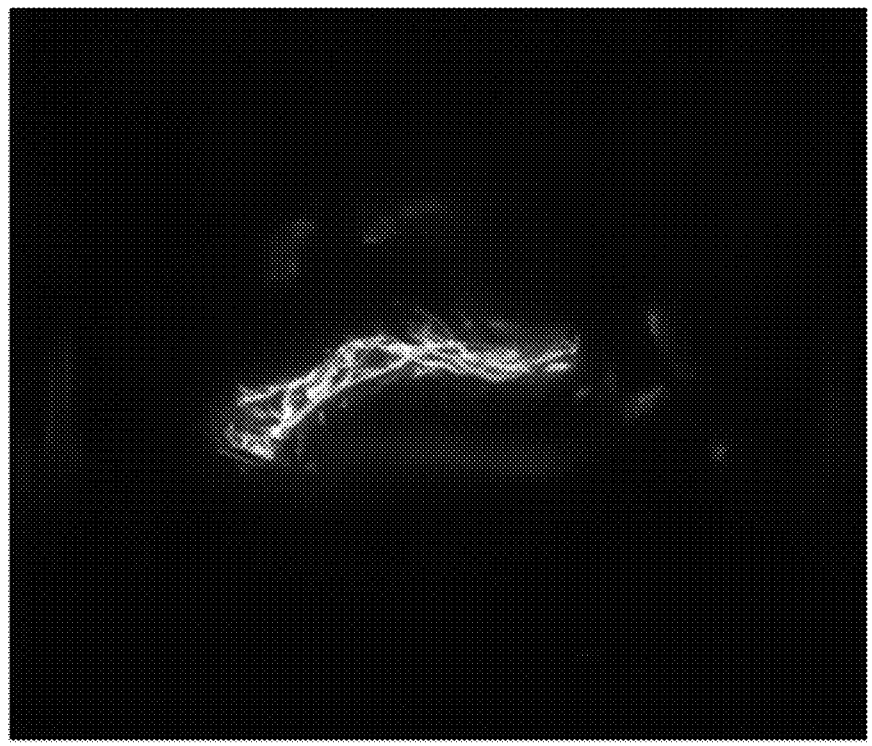
FIG. 8 is an image of streamer transitions to a spark discharge observed following a sufficient pulse length to generate the discharge.
Figure 9:
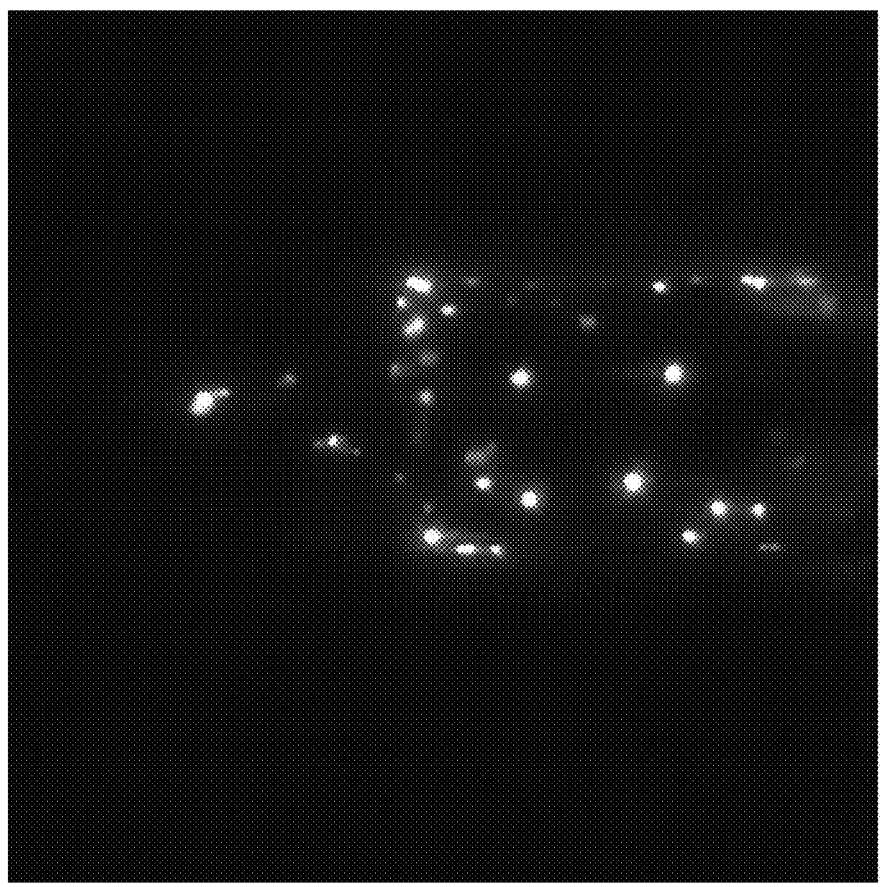
FIG. 9 is an image of multiple streamer discharges generated with a sharpened tungsten electrode covered in 560 nm of aluminum oxide deposited by atomic layer deposition in a saline solution.

Model electrodes were used to generate plasma discharges in aqueous liquids. FIG. 7 depicts a streamer plasma discharge in distilled water using a sharpened tungsten needle as an electrode. FIG. 8 depicts streamer transitions to a spark discharge in distilled water. Streamers produce a spark discharge at longer pulse lengths. FIG. 9 depicts multiple streamer discharges in a saline solution using a sharpened tungsten needle as an electrode. A dielectric coating is required in conducting liquids such as saline, and the tungsten needle was coated in 560 nm of aluminum oxide as a dielectric coating. The aluminum oxide was deposited by atomic layer deposition.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating a disease or condition in a subject, the method comprising:
   contacting the subject with a catheter comprising a lumen carrying a first electrode and a second electrode spaced apart from the first electrode by a dielectric;
   causing the first electrode, the second electrode and/or the dielectric to contact with a bodily fluid of the subject; and
   providing an electric current via the first electrode or the second electrode, thereby producing a localized, non-equilibrium plasma from the bodily fluid of the subject,
   wherein less than 1 mL of a gas is generated in the subject after providing the electric current and producing the localized, non-equilibrium plasma from the bodily fluid.

2. The method of claim 1, wherein the disease or condition is atherosclerosis or endocarditis.

3. The method of claim 1, wherein:
   the localized, non-equilibrium plasma ablates either a structure associated with the disease or condition or a portion of the structure;
   the localized, non-equilibrium plasma generates a reactive molecule or ion, and the reactive molecule or ion ablates either a structure associated with the disease or condition or a portion of the structure; or
   the localized, non-equilibrium plasma generates a therapeutic molecule, wherein the therapeutic molecule is toxic to a pathogen, the therapeutic molecule initiating intracellular signaling, or the therapeutic molecule has a physiological effect.

4. The method of claim 1, wherein:
   the localized, non-equilibrium plasma generates a reactive molecule or ion;
   the reactive molecule or ion ablates either a structure associated with the disease or condition or a portion of the structure; and
   the reactive molecule or ion is a reactive oxygen species (ROS) or a reactive nitrogen species (RNS).

5. The method of claim 4, wherein the ROS or RNS is selected from $H_2O_2$ (hydrogen peroxide), .OH (hydroxyl radical), $O_2^-$ (superoxide anion radical), $O_3$ (ozone), $.O_2$ (singlet oxygen), O (monomeric oxygen), $NO_2^-$ (nitrite), $NO_3^-$ (nitrate), nitric oxide (NO), and ONOO— (peroxynitrite).

6. The method of claim 4, wherein the structure comprises atheromatous plaque, fibroatheroma, arterial fibrosis, low-density lipoprotein (LDL) particles, a thrombus, fibrin, a calcium deposit, a tumor, malignant cells, cancerous cells, sarcoma, a virus, a parasite, a bacterium, or a bacterial biofilm.

7. The method of claim 1, wherein a temperature of the bodily fluid increases by more than 5° C. for a period of time less than 1 minute after the localized, non-equilibrium plasma is produced.

8. The method of claim 1, wherein producing the localized, non-equilibrium plasma does not generate an air embolism in the subject.

9. The method of claim 1, wherein the localized, non-equilibrium plasma comprises a series of localized, non-equilibrium plasmas with a repetition rate of 0.1 Hz to 20 kHz and a pulse-width of 10 ns to 1 µs.

10. The method of claim 1, wherein providing the electric current comprises providing the electric current at an operating-voltage of 1 kV to 30 kV.

11. The method of claim 1, wherein the non-equilibrium plasma has one or more of:
   an electron density greater than 1022 electrons per cubic meter;
   a power density greater than 1012 watts per cubic meter; and
   an electric field greater than 100 kV per cm.

12. The method of claim 1, wherein the localized, non-equilibrium plasma generates a local increase in pressure and/or the non-equilibrium plasma generates a shockwave in the bodily fluid.

13. The method of claim 1, wherein providing the electric current causes a spark discharge, a streamer discharge, or a corona discharge.

14. The method of claim 1, wherein causing the first electrode, the second electrode, and/or the dielectric to contact the bodily fluid further comprises causing the first electrode, the second electrode, and/or the dielectric to exit the lumen of the catheter via an aperture of the lumen and come into contact with the bodily fluid.

15. A method of treating a disease or condition in a subject, the method comprising:
   contacting the subject with a catheter comprising a distal aperture fluidly coupled to a lumen carrying a first electrode and a second electrode spaced apart from the first electrode by a dielectric;
   expelling the first electrode, the second electrode, and/or the dielectric from the lumen of the catheter through the distal aperture of the catheter into contact with a bodily fluid of the subject;
   providing an electric current via the first electrode or the second electrode, thereby producing a localized, non-equilibrium plasma from the bodily fluid of the subject, wherein less than 1 mL of a gas is generated in the subject after providing the electric current and producing the localized, non-equilibrium plasma from the bodily fluid; and
   retracting the one or more of the first electrode, the second electrode, and the dielectric into the lumen of the catheter through the distal aperture of the catheter.

16. The method of claim 15, wherein providing the electric current comprises providing the electric current at an operating-voltage of 1 kV to 30 kV.

\* \* \* \* \*